United States Patent
Kramer

(12) 
(10) Patent No.: US 6,685,721 B1
(45) Date of Patent: Feb. 3, 2004

(54) CATHETER SYSTEM WITH CATHETER AND GUIDEWIRE EXCHANGE

(75) Inventor: Barry L. Kramer, Chicago, IL (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1,826 days.

(21) Appl. No.: 07/881,673

(22) Filed: May 12, 1992

Related U.S. Application Data

(63) Continuation of application No. 07/713,973, filed on Jun. 11, 1991, now Pat. No. 5,135,535.

(51) Int. Cl.$^7$ .................. A61M 29/00; A61M 5/178

(52) U.S. Cl. ............... 606/194; 604/102.02; 604/160

(58) Field of Search .................. 606/192, 194, 606/195; 604/160, 282, 102, 161, 96; 128/657, 772

(56) References Cited

U.S. PATENT DOCUMENTS

| | | |
|---|---|---|
| 3,262,449 A | 7/1966 | Pannier et al. |
| 3,297,030 A | 1/1967 | Czorny et al. |
| 3,550,591 A | 12/1970 | MacGregor |
| 3,682,173 A | 8/1972 | Center |
| 3,853,130 A | 12/1974 | Sheridan |
| 4,037,599 A | 7/1977 | Raulerson |
| 4,054,136 A | 10/1977 | von Zeppelin |
| 4,079,738 A | 3/1978 | Dunn et al. |
| 4,147,165 A | 4/1979 | Tauschinski |
| 4,175,564 A | 11/1979 | Kwak |
| 4,323,071 A | 4/1982 | Simpson et al. |
| 4,411,055 A | 10/1983 | Simpson et al. |
| 4,411,654 A | 10/1983 | Boarini et al. |
| 4,439,185 A | 3/1984 | Lundquist |
| 4,468,224 A | 8/1984 | Enzmann et al. |
| RE31,855 E | 3/1985 | Osborne |
| 4,516,972 A | 5/1985 | Samson |
| 4,538,622 A | 9/1985 | Samson et al. |
| 4,554,929 A | 11/1985 | Samson et al. |
| 4,569,347 A | 2/1986 | Frisbie |
| 4,573,470 A | 3/1986 | Samson et al. |
| 4,581,017 A | 4/1986 | Sahota |

(List continued on next page.)

FOREIGN PATENT DOCUMENTS

| | | |
|---|---|---|
| EP | A-0 274 129 | 12/1987 |
| EP | A-0 282 143 | 1/1988 |
| EP | A-0 388 112 | 3/1990 |
| EP | 0416662 B1 | 3/1991 |
| WO | WO 82/03558 | 10/1982 |
| WO | WO 91/05512 | 5/1991 |
| WO | WO 92/17236 | 10/1992 |

OTHER PUBLICATIONS

Suggested Directions for Use, Outsider™ Ultra Low Profile Coronary Balloon Dilatation Catheter, Mansfield, Boston Scientific Corporation.

*Primary Examiner*—Cary E. O'Connor
(74) *Attorney, Agent, or Firm*—McAndrews, Held & Malloy, Ltd.

(57) ABSTRACT

An intravascular catheter system, such as a dilatation catheter system for angioplasty procedures, which provides for the replacement of the catheter or the guidewire thereof during the procedure. The intravascular catheter has an guidewire-receiving inner lumen extending along the length thereof. A first guidewire port is provided in the catheter body at or near the proximal end of the catheter, a second guidewire port is provided in the catheter body at a location spaced distally from the first guidewire port and proximally from a diagnostic or therapeutic element, such as a dilatation balloon, on a distal portion of the catheter and a third guidewire port is provided in the distal end of the catheter. The guidewire ports are in communication with the guidewire-receiving inner lumen.

4 Claims, 2 Drawing Sheets

U.S. PATENT DOCUMENTS

| | | | |
|---|---|---|---|
| 4,582,181 A | | 4/1986 | Samson |
| 4,585,013 A | | 4/1986 | Harris |
| 4,596,559 A | | 6/1986 | Fleischhacker |
| 4,616,652 A | | 10/1986 | Simpson |
| 4,619,644 A | | 10/1986 | Scott |
| 4,631,056 A | | 12/1986 | Dye |
| 4,631,059 A | | 12/1986 | Wolvek et al. |
| 4,638,805 A | | 1/1987 | Powell |
| 4,705,507 A | | 11/1987 | Boyles |
| 4,723,948 A | | 2/1988 | Clark et al. |
| 4,738,666 A | | 4/1988 | Fuqua |
| 4,747,833 A | | 5/1988 | Kousai et al. |
| 4,748,982 A | * | 6/1988 | Horzewski et al. ......... 606/192 |
| 4,748,986 A | | 6/1988 | Morrison et al. |
| 4,762,129 A | | 8/1988 | Bonzel |
| 4,771,777 A | | 9/1988 | Horzewski et al. |
| 4,813,930 A | | 3/1989 | Elliott |
| 4,821,722 A | | 4/1989 | Miller et al. |
| 4,865,593 A | | 9/1989 | Ogawa et al. .............. 604/264 |
| 4,883,468 A | | 11/1989 | Kousai et al. |
| 4,888,000 A | | 12/1989 | McQuilkin et al. |
| 4,898,577 A | | 2/1990 | Badger et al. |
| 4,931,049 A | | 6/1990 | Klimas |
| 4,944,745 A | * | 7/1990 | Sogard et al. .............. 606/194 |
| 4,947,864 A | * | 8/1990 | Shockey et al. ............ 128/657 |
| 4,981,478 A | | 1/1991 | Evard et al. |
| 4,988,356 A | | 1/1991 | Crittenden et al. |
| 4,997,424 A | | 3/1991 | Little |
| 5,024,234 A | * | 6/1991 | Leary et al. ............. 128/663.1 |
| 5,034,001 A | | 7/1991 | Garrison et al. |
| 5,046,503 A | | 9/1991 | Schneiderman |
| 5,061,267 A | | 10/1991 | Zeiher |
| 5,061,273 A | | 10/1991 | Yock |
| 5,102,403 A | | 4/1992 | Alt |
| 5,135,482 A | * | 8/1992 | Neracher ................... 606/159 |
| 5,154,725 A | | 10/1992 | Leopold |
| 5,171,222 A | | 12/1992 | Euteneuer et al. |
| 5,195,978 A | | 3/1993 | Schiffer |
| 5,205,822 A | | 4/1993 | Johnson et al. |
| 5,267,982 A | | 12/1993 | Sylvanowicz |
| 5,395,335 A | | 3/1995 | Jang |

* cited by examiner

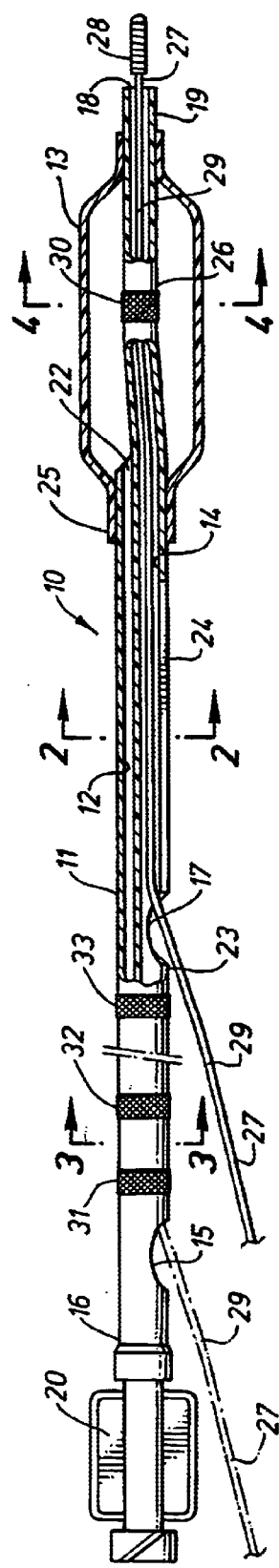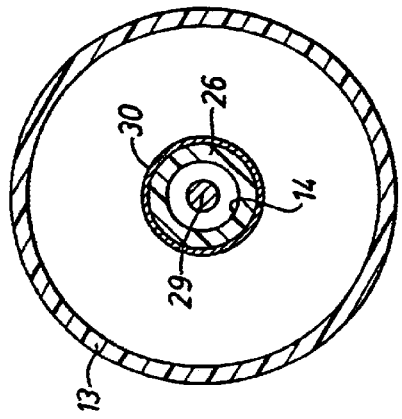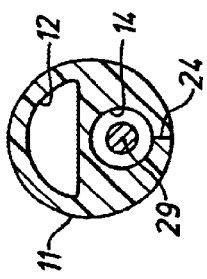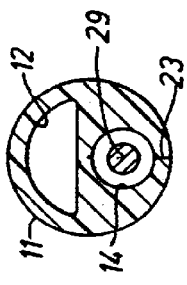

CATHETER SYSTEM WITH CATHETER AND GUIDEWIRE EXCHANGE

This is a continuation of the application Ser. No. 07/713,973 which was filed on Jun. 11, 1991, now U.S. Pat. No. 5,135,535.

BACKGROUND OF THE INVENTION

This invention generally relates to a catheter system which is suitable for intravascular procedures such as percutaneous transluminal coronary angioplasty (PTCA) and which allows for the exchange of guidewires and catheters during such procedures.

In classic PICA procedures, a guiding catheter having a preshaped distal tip is percutaneously introduced into the cardiovascular system of a patient and advanced therein until the preshaped distal tip thereof is disposed within the aorta adjacent the ostium of the desired coronary artery. The guiding catheter is twisted or torqued from the proximal end to turn the distal tip of the guiding catheter so that it can be guided into the coronary ostium. A dilatation catheter having a balloon on the distal end thereof and a guidewire slidably disposed within an inner lumen of the dilatation catheter are introduced into and advanced through the guiding catheter to the distal tip thereof. The distal tip of the guidewire is usually manually shaped (i.e. curved) by the physician or one of the attendants before the guidewire is introduced into the guiding catheter along with the dilatation catheter. The guidewire is first advanced out the distal tip of the guiding catheter, which is seated in the ostium of the patient's coronary artery, into the patient's coronary artery. A torque is applied to the proximal end of the guidewire, which extends out of the patient, to guide the curved or otherwise shaped distal end of the guidewire as the guidewire is advanced within the coronary anatomy until the shaped distal end of the guidewire enters the desired artery. The advancement of the guidewire within the selected artery continues until it crosses the lesion to be dilated. The dilatation catheter is then advanced out of the distal tip of the guiding catheter, over the previously advanced guidewire, until the balloon on the distal extremity of the dilatation catheter is properly positioned across the lesion. Once properly positioned, the flexible, relatively inelastic balloon is inflated to a predetermined size with radiopaque liquid at relatively high pressures (e.g., 4–12 atmospheres) to dilate the stenosed region of the diseased artery. The balloon is then deflated so that the dilatation catheter can be removed from the dilated stenosis and blood flow can then be resumed therethrough.

Further details of guiding catheters, dilatation catheters, guidewires, and the like for angioplasty procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson); U.S. Pat. No. 4,438,622 (Samson et al.); U.S. Pat. No. 4,554,929 (Samson et al.); U.S. Pat. No. 4,582,185 (Samson); U.S. Pat. No. 4,616,652 (Simpson); U.S. Pat. No. 4,638,805 (Powell); U.S. Pat. No. 4,748,986 (Morrison et al.); U.S. Pat. No. 4,898,577 (Badger et al.); and U.S. Pat. No. 4,748,982 (Horzewski et al.) which are hereby incorporated herein in their entirety by reference thereto.

Recently, the licensee of the present invention, Advanced Cardiovascular Systems, Inc., introduced into the market place an improved dilatation catheter which is described and claimed in copending application Ser. No. 07/550,801 (Yock), filed Jul. 9, 1990 and U.S. Pat. No. 4,748,982 (Horzewski et al.). This dilatation catheter has a short guidewire-receiving sleeve or inner lumen extending through just the distal portion of the catheter. The sleeve extends proximally at least 10 cm, typically about 25 cm, from a guidewire port in the distal end of the catheter to another guidewire port in the wall of the catheter. A slit is provided in the catheter wall which extends distally from the second guidewire port to a location proximal to the proximal end of the inflatable balloon. The structure of the catheter allows for the rapid exchange of the catheter without the need for an exchange wire or adding a guidewire extension to the proximal end of the guidewire.

The catheter design embodying the Yock and Horzewski et al. improvements has been widely praised by members of the medical profession and has met with much commercial success in the market place. Nonetheless, there are some inconveniences in its use because the catheter does not allow for the exchange or replacement of the guidewire. For example, the shaped distal tip of the guidewire may become deformed in use or the shape of the distal tip or the size of the guidewire may be found to be no longer suitable for the particular procedure within the patient's vasculature. In this instance the physician might want to remove the guidewire and reshape the distal tip or replace the first guidewire with another having the desired size, stiffness or shape. However, when the guidewire in a dilatation catheter system embodying the Yock and Horzewski et al. improvements is removed, access to the desired arterial location through the distal guidewire lumen of the catheter is lost. Unfortunately, there is no way to clinically determine before the guidewire is inserted into the patient in an angioplasty procedure whether a guidewire or a catheter will have to be exchanged during the procedure.

What has been needed and heretofore unavailable is an intravascular catheter system which allows for the rapid exchange of either the catheter or the guidewire during an intravascular procedure without losing access to the desired region of the patient's arterial system. The present invention satisfies this and other needs.

SUMMARY OF THE INVENTION

This invention is directed to a catheter system which can be used in an over-the-wire type mode and which can also allow for the exchange of either a guidewire or a catheter mounted over a guidewire during an intraluminal procedure such as PTCA without losing access to the body lumen and the method of using such a catheter system.

The catheter system of the invention generally comprises an elongated catheter body with proximal and distal ends, a diagnostic or therapeutic means, such as an inflatable balloon positioned on a distal portion of the body and a guidewire-receiving inner lumen extending within the body to the distal end thereof. The catheter body has a first guidewire port at or near the proximal end thereof, a second guidewire port in the catheter body between the first port and the diagnostic or therapeutic means, and a third guidewire port in the distal end of the catheter, all of which are in communication with the guidewire-receiving inner lumen within the catheter body. The first port is generally at or close to the proximal end of the catheter body, e.g. not more than about 30 cm therefrom, and, preferably, is not more than about 10 cm from the proximal end of the catheter body. The second port is spaced closer to the diagnostic or therapeutic means than it is to the first port and generally is at least about 10 cm from the distal end of the catheter body preferably about 15 cm to about 40 cm.

In a presently preferred embodiment the catheter is a balloon dilatation catheter adapted to perform PTCA procedures. The catheter has a catheter body with two inner lumen extending essentially the length thereof, one of the lumens being a guidewire-receiving lumen and the other lumen being adapted to direct inflation fluid to the interior of a dilatation balloon on the distal portion of the catheter. One of the attractive features of this catheter design is that the catheter can be used as an over-the-wire type dilatation catheter in a conventional fashion, yet it allows both the catheter and the guidewire to be exchanged during the PTCA procedure. Similar catheter designs can be used with other intraluminal catheters which have diagnostic or therapeutic means on the distal portion of the catheter.

To facilitate the separation of the guidewire and the catheter during an exchange thereof, a slit is preferably provided in the wall of the catheter body which defines at least part of the guidewire-receiving inner lumen. The slit extends distally from the first guidewire port, preferably to the second port. A second slit should extend distally from the second guidewire port to a location proximately adjacent the diagnostic or therapeutic means.

To replace a catheter during an intraluminal procedure such as PTCA, the in-place catheter is pulled proximally over the guidewire from the proximal end of the catheter. If the in-place guidewire extends out the second guidewire port, the catheter is withdrawn peeling the catheter off of the guidewire through the slit extending distally from the second guidewire until the distal end of the catheter exits the proximal end of the guiding catheter or an adapter attached thereto at which point the guidewire can be manually held in position while the catheter is removed from the proximal end thereof. If the in-place guidewire exits the inner lumen of the catheter from the first guidewire port, the catheter is separated from the guidewire by peeling the catheter away from the guidewire through the slit which extends between the first and second guidewire port as the catheter is withdrawn from the proximal end of the guiding catheter or the adapter attached thereto until the guidewire exits the second guidewire port. The separation of the catheter from the guidewire continues as previously described with the catheter being peeled off of the guidewire through the slit which extends distally from the second guidewire port. The catheter is further withdrawn until the distal end of the catheter exits the proximal end of the guiding catheter and which time the guidewire can be manually held while the catheter is pulled off the proximal end of the guidewire.

Once the catheter has been removed from the proximal end of the in-place guidewire, the proximal end of the in-place guidewire is inserted into the third guidewire port in the distal end of a replacement catheter and then the replacement catheter can be advanced into the patient's vasculature over the in-place guidewire to perform the intravascular procedure. The proximal end of the guidewire can be directed out of either the second or the first guidewire port in the catheter body depending upon the needs of the physician.

The catheter system of the invention also allows for the exchange of an in-place guidewire during an intraluminal procedure while holding the catheter in place so as to maintain access to the intraluminal position. To replace an in-place guidewire, it is removed from the guidewire-receiving inner lumen of the catheter and the patient by pulling on its proximal end which extends out of the patient. When the in-place guidewire is removed from the inner lumen of the in-place catheter, the replacement guidewire is inserted into the guidewire-receiving inner lumen of the in-place catheter through the proximal guidewire port and advanced through the guidewire-receiving inner lumen and out the third port in the distal end thereof to the desired location within the patient's body lumen. If the in-place guidewire extends out the second guidewire port, it may be desirable to have the replacement guidewire inserted into the proximal portion of the guidewire-receiving inner lumen through the first or proximal guidewire port before the in-place guidewire is removed from the distal portion of the inner lumen so that there is little chance of losing access to the lumenal location by the accidental movement of the in-place catheter. When the replacement guidewire is advanced through the in-place catheter and properly positioned in a desired location therein, e.g. across a stenosis in a patient's artery which is to be dilated, the catheter may then be advanced over the replacement guidewire to the desired location so as to perform the desired diagnostic or therapeutic treatment therein.

The intravascular catheter of the invention also allows for the removal and reinsertion of a guidewire, for example, when the physician wishes to change the shape of the distal end of a guidewire during a procedure. In this operative modality, the in-place guidewire can be withdrawn in essentially the manner described above, the distal tip thereof reshaped and then be reintroduced into the in-place catheter in essentially the same manner as described above.

As will become more apparent from the following detailed description of the invention, the intravascular catheter system of the invention allows for a wide variety of intravascular procedures which were heretofore impossible to perform with a single catheter system. These and other advantages are described in the following detailed description when taken in conjunction with the accompanying exemplary drawings.

BRIEF DESCRIPTION OF THE DRAWINGS

FIG. 1 is an elevational view, partially in section, of a dilatation catheter having a guidewire-receiving inner lumen which embodies features of the invention.

FIG. 2 is a transverse, cross-sectional view of the catheter shown in FIG. 1 taken along the lines 2—2.

FIG. 3 is a transverse, cross-sectional view of the catheter shown in FIG. 1 taken along the lines 3—3.

FIG. 4 is a transverse, cross-sectional view of the catheter shown is FIG. 1 taken along the lines 4—4.

DETAILED DESCRIPTION OF THE INVENTION

Figure 5:
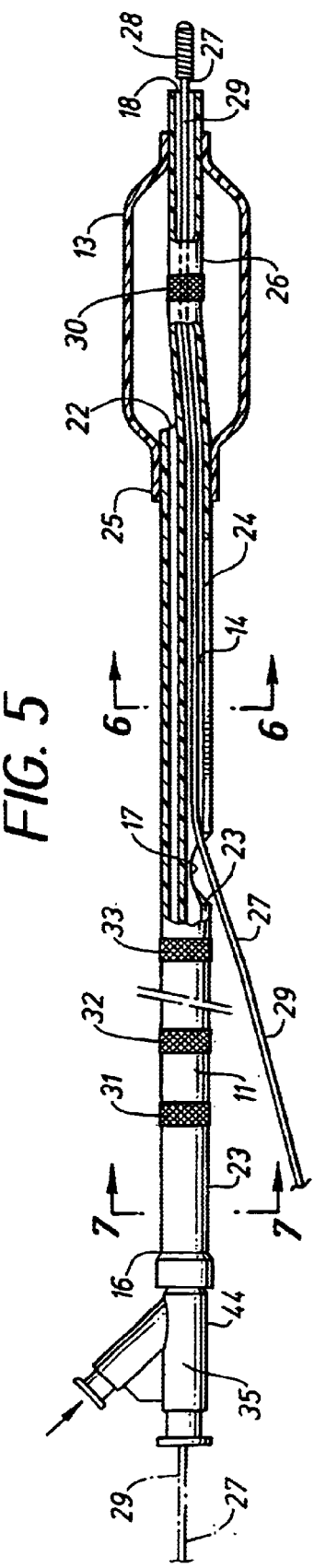
FIG. 5 illustrates an alternate embodiment of the invention in which a guidewire extends out the proximal end of an adapter mounted on the proximal end of the catheter body.

FIGS. 1–4 illustrate a dilatation catheter 10 embodying features of the invention which allow for the exchange of a guidewire while the catheter remains in place within the patient and which also allow for the exchange of the catheter while the guidewire remains in place so as to avoid loss of the arterial position. The catheter 10 generally comprises an elongated catheter body 11, an inflation lumen 12 adapted to direct inflation fluid from the proximal end of the catheter body, to the interior of an inflatable balloon 13 on the distal portion of the catheter body and a guidewire-receiving inner lumen 14 extending therein.

The wall of the catheter body 11 defining at least part of the guidewire-receiving inner lumen 14 has a first guidewire port 15 near the proximal end 16 of the catheter body, a second guidewire port 17 distal to the first port and at least about 10 cm from the distal end of the catheter body and a third guidewire port 18 located in the distal end 19 of the catheter body, wherein the second guidewire port 17 is substantially closer to the third port 18 than the first port 15.

An adapter 20 is provided on the proximal end 16 of the catheter body 11 to facilitate the introduction of inflation fluid into the inflation lumen 12 which directs the fluid to the interior of the inflatable balloon 13 through the inflation port 22.

A first slit 23 is preferably provided in the wall of the catheter body which defines the guidewire-receiving inner lumen 14 and extends between the first guidewire port 15 and the second guidewire port 17. A second slit 24 is provided in the wall of the catheter body 11 which further defines the guidewire-receiving inner lumen and extends from the second guidewire port 17 to a location proximal to the proximal end 25 of the balloon 13.

The catheter body 11 has a tubular extension 26 on the distal portion thereof which extends through the interior and out the distal end of the balloon 13. The tubular extension 26 is adapted to receive a guidewire 27 within the inner lumen 14. The distal end of the guidewire 27 has a coil 28 on the distal end thereof which is shown extending out the third guidewire port 18 in the distal end 19 of the catheter body 11 and has an elongated core member 29 which is shown extending out the second guidewire port 18. The guidewire 27 is shown in phantom in a second position disposed within the proximal section of the inner lumen 14. The proximal portion of the elongated core member 29 extends out the first guidewire port 15 near the proximal end 16 of the catheter body 11.

A radiopaque marker 30 is disposed about the tubular extension 26 within the interior of the balloon 13 to facilitate the fluoroscopic observation thereof during an intravascular procedure. Radiopaque markers 31, 32 and 33 may also be provided on the proximal portion of the catheter body 11 to allow the physician to fluoroscopically determine the location of the first and second guidewire ports and the like during the intravascular procedures.

The catheter system of the invention can be inserted into the patient in a conventional over-the-wire fashion with the guidewire 27 preloaded within the inner lumen 14 and extending proximally out the first or proximal port 15 or it can be inserted in a manner similar to that used to insert catheters having the improvements of Yock and Horzewski et al. wherein the guidewire extends proximally out the second or intermediate guidewire port 17. When it becomes desirable or necessary at any time during the intravascular procedure to remove or replace either the catheter 10 or the guidewire 27 either may be removed by pulling on the proximal end thereof which extends out of the patient while the catheter or guidewire which remains within the patient is held in position in order to maintain access to the desired intravascular location.

If the guidewire is to be removed, the catheter 10 is held in place while the guidewire is pulled out of the proximal end of the guiding catheter and the catheter 10. When the guidewire has been removed from the catheter 10, a replacement guidewire may then be inserted through the first guidewire port 15 which is outside the patient into the inner lumen 14 and advanced therein until the guidewire exits the third guidewire port 18 in the distal end 19 of the catheter body 11 into the patient's coronary artery. Once the replacement guidewire 27 is properly positioned within the patient's artery, e.g. across a stenosis to be dilated, the dilatation catheter 10 may then be further advanced within the artery over the replacement guidewire to the desired location therein to perform the dilatation or other diagnostic or therapeutic procedure in a conventional manner.

If the catheter 10 is to be removed and the guidewire 27 extends proximally out the first guidewire port 15, the guidewire and the catheter are separated while the catheter is being removed by pulling the guidewire through the slit 23 until the guidewire extends out the second guidewire port 17. The peeling of the catheter off of the guidewire 27 continues through the slit 24 while the catheter is being withdrawn. When the distal end 19 of the catheter exits the proximal end of the guiding catheter, the guidewire may be manually gripped and the catheter 10 removed from the proximal end of the guidewire. If the guidewire 27 exits the second guidewire port 17 the procedure is essentially the same except that there is no need to peel the catheter 10 away from the guidewire through the slit 23 until the guidewire extends through the second guidewire port 17. When the catheter 10 has been removed, the replacement catheter is mounted onto the guidewire 27 by inserting the proximal end of the guidewire through the third guidewire port 18 in the distal end 19 of the replacement catheter and advancing the catheter over the guidewire disposed within the inner lumen 14 of the catheter until the guidewire exits the secondguidewire port 17. The replacement catheter may then be inserted into the patient and advanced therein in a conventional manner as described in Yock or Horzewski et al. which have been incorporated herein.

In another method the replacement catheter is mounted onto the guidewire 27 as previously described but the replacement catheter is advanced over the guidewire until the proximal end of the guidewire exits the first guidewire port 15. In this method the replacement catheter is advanced well within the patient's vasculature before the guidewire exits the proximal end of the guidewire exits the first port, it is manually grasped and the replacement catheter advanced further over the wire into the patient's coronary arteries.

Figure 6:
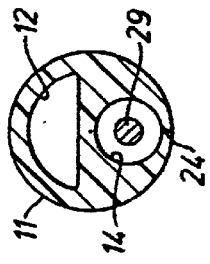
FIG. 6 is a transverse, cross-sectional view of the catheter shown in FIG. 5 taken along the lines 6—6.
Figure 7:
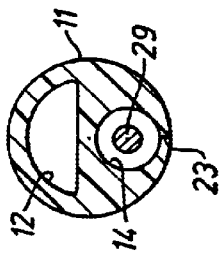
FIG. 7 ia a transverse, cross-sectional view of the catheter shown in FIG. 5 taken along the lines 7—7.

An alternate embodiment of the invention is illustrated in FIGS. 5–7. This embodiment is quite similar to the embodiment shown is FIGS. 1–4 except that the guidewire 27 extends through the center arm of the two arm adaptor 35 on the proximal end of the catheter body 11. The corresponding parts of this embodiment are numbered the same as the parts of the embodiments shown in FIGS. 1–4. The first guidewire port 15 in this embodiment (not shown in the drawings) is in the proximal end 16 of the catheter body 11 and opens to the adapter 35. The use of this embodiment is the essentially the same as the embodiment shown in FIGS. 1–4. The adaptor 35 is modified to include a slit 44 which is continuous with the slit 23 in the catheter body 11.

The catheter body 11 can be formed by conventional techniques, e.g. extruding, from materials already found useful in intravascular catheters such a polyethylene, polyimide, polyvinyl chloride, polyesters and composite materials such as described in U.S. Pat. No. 4,981,478 (Evard et al.) which is incorporated herein by reference. The various components of the catheter can be joined by suitable adhesive such as the acrylonitrile based adhesive sold as Loctite™ 405. Heat shrinking may also be employed where appropriate. A venting means may be provided to remove air from the interior of the balloon before the catheter is inserted into the patient such as described in U.S. Pat. No. 4,638,805

(Powell) and U.S. Pat. No. 4,821,722 (Samson et al.) which have been incorporated herein.

The size of the catheter body 11 and the guidewire-receiving inner lumen 14 thereof to a large extent are determined by the size of the guidewires 27 to be employed and the size of the artery or other body lumen through which the catheter must pass. Generally, the diameter of the inner lumen is sufficient to accommodate the guidewire and to allow it to be slidably disposed therein. The diameters of guidewires for coronary use can vary from about 0.008 to about 0.035 inch (0.2–0.89 mm) in diameter, and the inner diameter of the guidewire-receiving inner lumen 14 of the catheter 10 should be about 0.001 to about 0.005 inch (0.025–0.127 mm) larger than the diameter of the guidewire. The catheter body 11 is sufficiently long to extend from outside the proximal end of a guiding catheter, which likewise extends out of the patient, to a stenosis to be treated within the patient's vascular system (or other desired location therein), e.g. from about 100 to about 150 cm when a Seldinger approach through the femoral artery is employed to introduce the catheter 10 into the patient's vasculature. The wall forming the catheter must be of sufficient thickness and strength so that it can be pushed over the guidewire 27 to the desired location within the patient's blood vessel. If desired the proximal portion of the dilatation catheter 10 can be provided with a stiffening means to facilitate the advancement of the catheter within the patient's vasculature.

While the invention has been described herein in terms of certain presently preferred embodiments directed to balloon dilatation catheters for use in coronary angioplasty procedures, those skilled in the art will recognize that the catheter of the invention may be used in a variety of body lumens. For example, the invention can be utilized in a wide variety of diagnostic and therapeutic intravascular catheters. Additionally, the catheter body may be of concentric construction rather than the dual lumen construction shown herein. Other modifications and improvements may be made to the invention without departing from the scope thereof.

What is claimed is:

1. A readily exchangeable dilatation catheter suitable for performing angioplasty procedures within a patient's artery which permits the exchange of a guidewire during an angioplasty procedure, comprising:
   a) an elongated catheter body having proximal and distal ends, a first lumen adapted to receive a guidewire and extending within the catheter body to the distal end thereof and a second lumen adapted to direct inflation fluid therethrough and extending parallel to and offset from the first lumen within the catheter body to a distal portion thereof;
   b) an inflatable member on a distal portion of the catheter body having an interior in fluid communication with the second lumen;
   c) a first guidewire port in the catheter body being located at or near the proximal end of the catheter body and being in communication with the first lumen;
   d) a second guidewire port in a wall of the catheter body being spaced proximally from the inflatable member and distally a substantial distance from the proximal end and being in communication with the first lumen;
   e) a third guidewire port in the distal end of the catheter body distal to the inflatable member which is in communication with the first lumen; and
   f) means on the proximal end of the catheter body to direct inflation fluid to the interior of the inflatable member through the second lumen;
   wherein a slit is provided through the wall of the catheter body which extends between the first and the second guidewire ports and which is in communication with the first lumen.

2. The dilatation catheter of claim 1 wherein a second slit is provided in the wall of the catheter body which extends between the second guidewire port and a location proximally adjacent to the proximal end of the inflatable member and which is in communication with the first lumen.

3. A balloon dilatation catheter having proximal and distal ends, which comprises:
   a flexible, tubular catheter shaft which carries a dilatation balloon adjacent the distal end;
   said catheter shaft defining an inflation lumen communicating with said balloon; and
   a guidewire lumen extending at least most of the length of said catheter and extending through the catheter distal end;
   a longitudinal slit defined in said catheter shaft between the guidewire lumen and the catheter exterior, said slit extending longitudinally along the majority of the catheter length from a position proximal of said balloon to a position that is at least adjacent the catheter proximal end;
   in which said catheter shaft carries a hub at said proximal end, said hub defining a conduit connecting with said guidewire lumen, said slit of the catheter shaft extending to said hub; and
   a longitudinal slot extending the length of said hub in communication between said hub conduit and the hub exterior, said slot also being aligned with said slit to permit a sliding member in said slot to slide into said slit.

4. A method of exchanging a catheter during a procedure involving vascular catheterization, comprising the steps of:
   a) providing first and second angioplasty catheters comprising:
      i. a catheter shaft having a proximal end and a distal end;
      ii. an angioplasty balloon attached to said shaft at said distal end;
      iii. a balloon inflation lumen extending through said shaft and communicating with the interior of said balloon; and
      iv. a guidewire lumen extending through said shaft and through said balloon for receiving a steerable guidewire, wherein said guidewire lumen has a proximal opening at the proximal end of said shaft for insertion of a guidewire into said lumen, a side port for passage of a guidewire into said lumen through the side of a said catheter shaft, said side port located distally of said proximal opening, and a distal opening located distally of said side opening;
      v. said first catheter having a guidewire passing through said guidewire lumen from the proximal opening to the distal opening thereof a positioning said catheter in a patient;
   b) removing said catheter from said patient while maintaining said guidewire in said patient;
   c) positioning said second catheter on said guidewire so that said guidewire passes through said side port and is inside said guidewire lumen distally of said side port and outside said guidewire lumen proximally of said side port; and
   d) advancing said second catheter along said guidewire into said patient while maintaining the positioning of the guidewire.

* * * * *